US00PP18485P3

(12) United States Plant Patent
Khanizadeh

(10) Patent No.: US PP18,485 P3
(45) Date of Patent: Feb. 12, 2008

(54) NON-BROWNING APPLE CULTIVAR NAMED 'SJCA38R6A74'

(50) Latin Name: *Malus×domestica*
Varietal Denomination: SJCA38R6A74

(75) Inventor: Shahrokh Khanizadeh, Baie d'Urfe (CA)

(73) Assignee: Her Majesty the Queen in Right of Canada as represented by the Minister of Agriculture and Agri-Food Canada, St.-Jean-sur-Richelieu (CA)

( * ) Notice: Subject to any disclaimer, the term of this patent is extended or adjusted under 35 U.S.C. 154(b) by 148 days.

(21) Appl. No.: 11/154,688

(22) Filed: Jun. 17, 2005

(65) Prior Publication Data

US 2006/0053517 P1 Mar. 9, 2006

(30) Foreign Application Priority Data

Sep. 8, 2004 (CA) ..... 04-4344

(51) Int. Cl.
*A01H 5/00* (2006.01)

(52) U.S. Cl. ..... Plt./161

(58) Field of Classification Search ..... Plt./161
See application file for complete search history.

*Primary Examiner*—Anne Marie Grunberg
*Assistant Examiner*—Annette H Para
(74) *Attorney, Agent, or Firm*—Goudreau Gage Dubuc

(57) ABSTRACT

A new and distinct apple tree cultivar named 'SJCA38R6A74' is primarily adapted to the growing conditions of Northern Eastern Central Canada. The fruit of 'SJCA38R6A74', which hangs well on tree, is a dessert apple having very good firmness, crispness and flavor, high quality flesh and a long shelf life. The phenol (oxidative agent) content of this cultivar's fruit is significantly lower than that of other known cultivars, including Cortland which is the most popular apple variety for transformation. No browning of the fruit occurs after cutting (even after 4–5 days at room temperature), without adding any chemical, which makes it an excellent candidate for fresh fruit slice, fruit salad, dried apple chips and processing (juice, cider).

7 Drawing Sheets

STATEMENT REGARDING FEDERALLY-SPONSORED RESEARCH AND DEVELOPMENT

None.

PRIORITY CLAIM

This application claims priority under 35 USC 199(f) of Plant Breeder's Rights application No. 04-4344 filed Sep. 8, 2004 in Canada.

FIELD OF THE INVENTION

The present invention relates to a new and distinct apple cultivar designated as 'SJCA38R6A74'. This cultivar belongs to the genus *Malus×domestica.*

BACKGROUND OF THE INVENTION

The new cultivar 'SJCA38R6A74', also tested as A38R6A38, originated from a cross between 'Linda' and NY44428-5 (Jonamac), (FIG. 1). 'SJCA38R6A74' was asexually reproduced by grafting on selected rootstocks in L'Acadie and Frelighsburg in Quebec, and has been under evaluation since 1985 in replicated trails.

The fruit, leave and tree morphology of 'SJCA38R6A74' were stable during the evaluation period in Quebec (Frelighsburg and Acadie). 'SJCA38R6A74' is now an established and stable cultivar.

'SJCA38R6A74' is similar to its parents in terms of fruit size, tree vigor and harvest date. However, 'SJCA38R6A74' is distinguishable from its parents in several respects e.g. fruit over, blush and ground color, fruit shape, tree growing habit which is spreading drooping, in opposition with Linda (upright) and Jonamac (upright spreading). Furthermore, the fruits of 'SJCA38R6A74' are persistent and do not fall at maturity even after freezing at −20° C. in February (FIG. 7), contrary to its parents, of which some fruits drop at maturity and do not stay on tree after freezing.

BRIEF SUMMARY OF THE INVENTION

'SJCA38R6A74' is adapted to the Northern climate and growing conditions similar to those of Frelighsburg and L'Acadie, Quebec.

'SJCA38R6A74' is a dessert apple (*domestica* Borkh.) type with improved firmness, crispness, high quality flesh and much longer shelf life than McIntosh and Cortland. The fruit flavor is pronounced and the fruits hang well on tree. The flesh is juicy, firm, crisp and resistant to bruising. The phenol (oxidative agent) content of the fruit is significantly less than the other known cultivars, even of Cortland which is the most popular apple variety for transformation and production of apple chips and fruit salad. No browning of the fruit occurs after cutting (even after 4–5 days at room temperature), without adding any chemical, which makes it an excellent candidate for fresh fruit slice, fruit salad, dried apple chips and processing (juice, cider).

BRIEF DESCRIPTION OF THE DRAWINGS

The accompanying color photographs show typical specimens of the new variety at various stages of development as nearly true as it is possible to make in color reproductions.

DETAILED BOTANICAL DESCRIPTION

Figure 1:
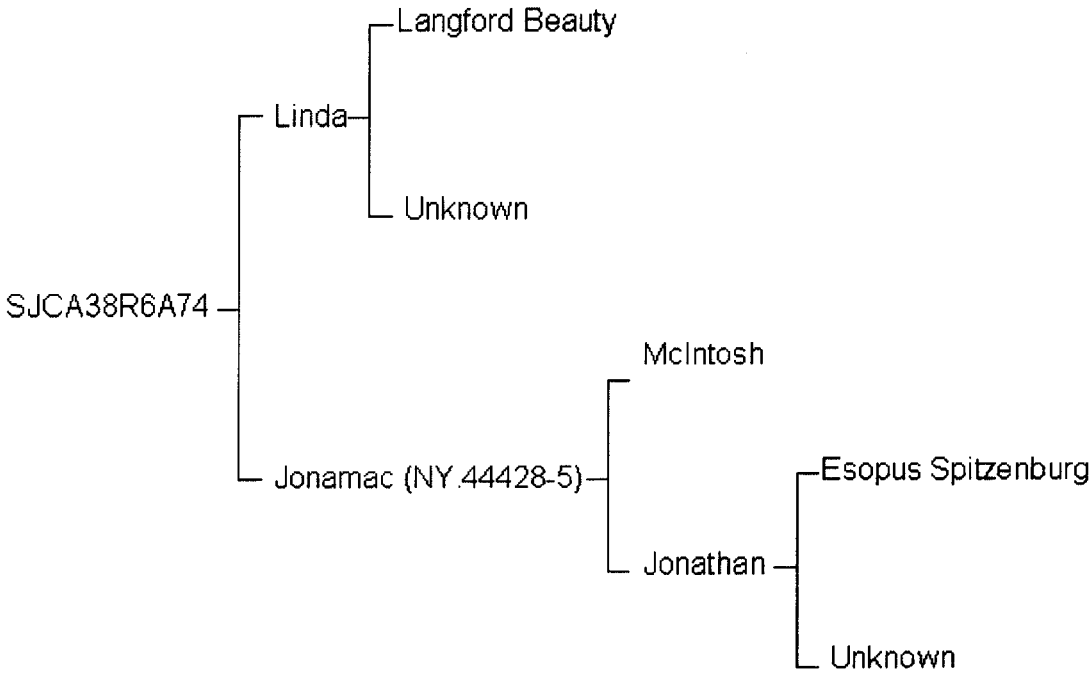
FIG. 1 schematically shows the pedigree of 'SJCA38R6A74'.
Figure 2:
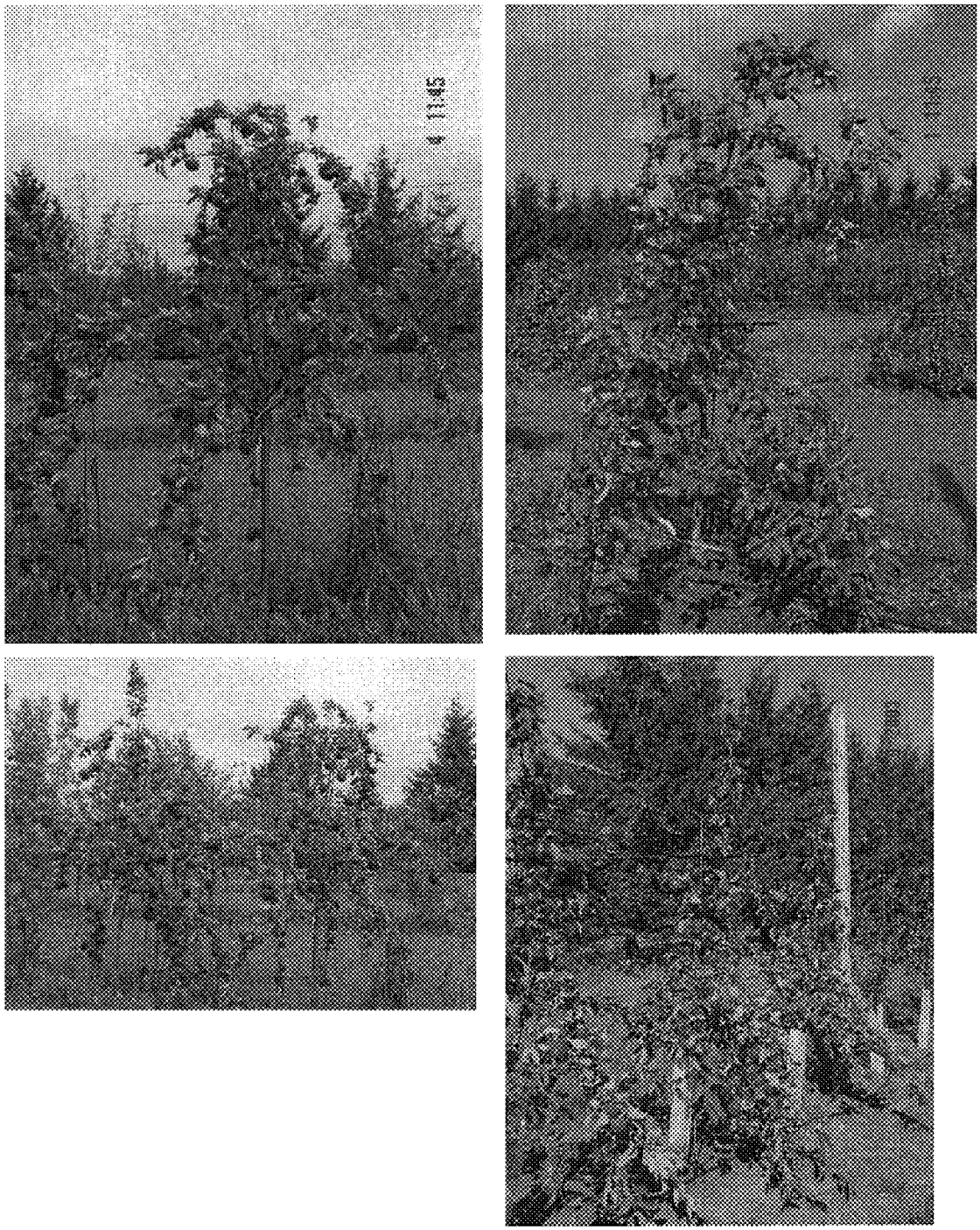
FIG. 2 shows tree of 'SJCA38R6A74' selection.
Figure 3:
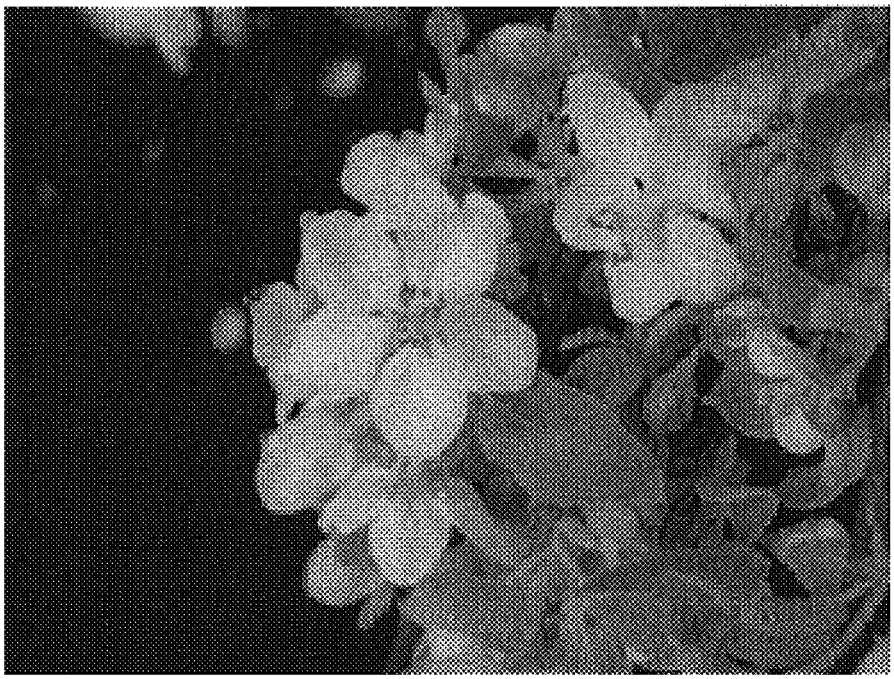
FIG. 3 shows the flowers of 'SJCA38R6A74'.
Figure 4:
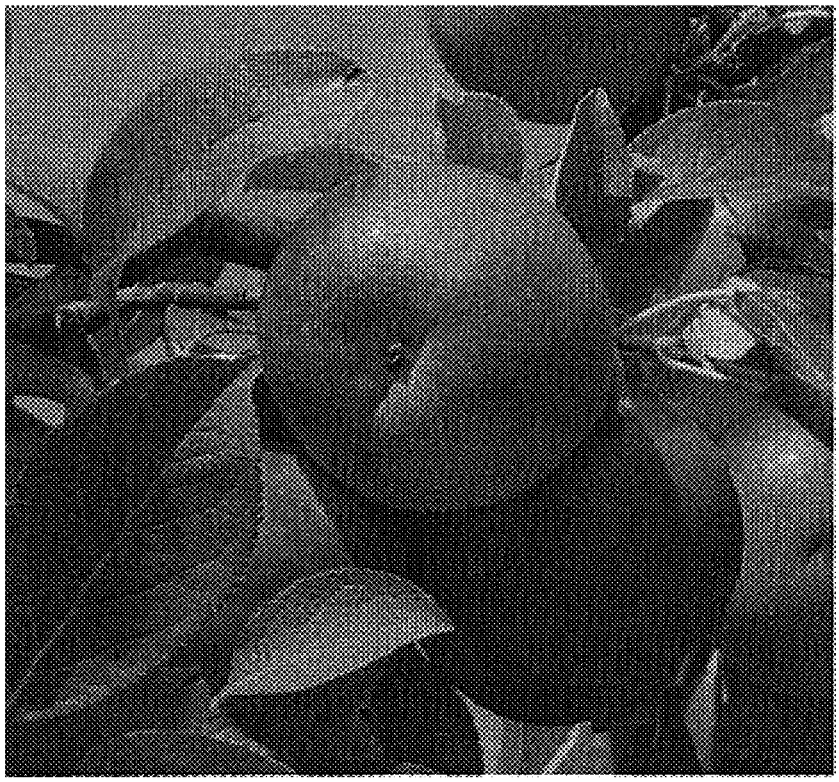
FIG. 4 shows the fruit of 'SJCA38R6A74'.
Figure 5:
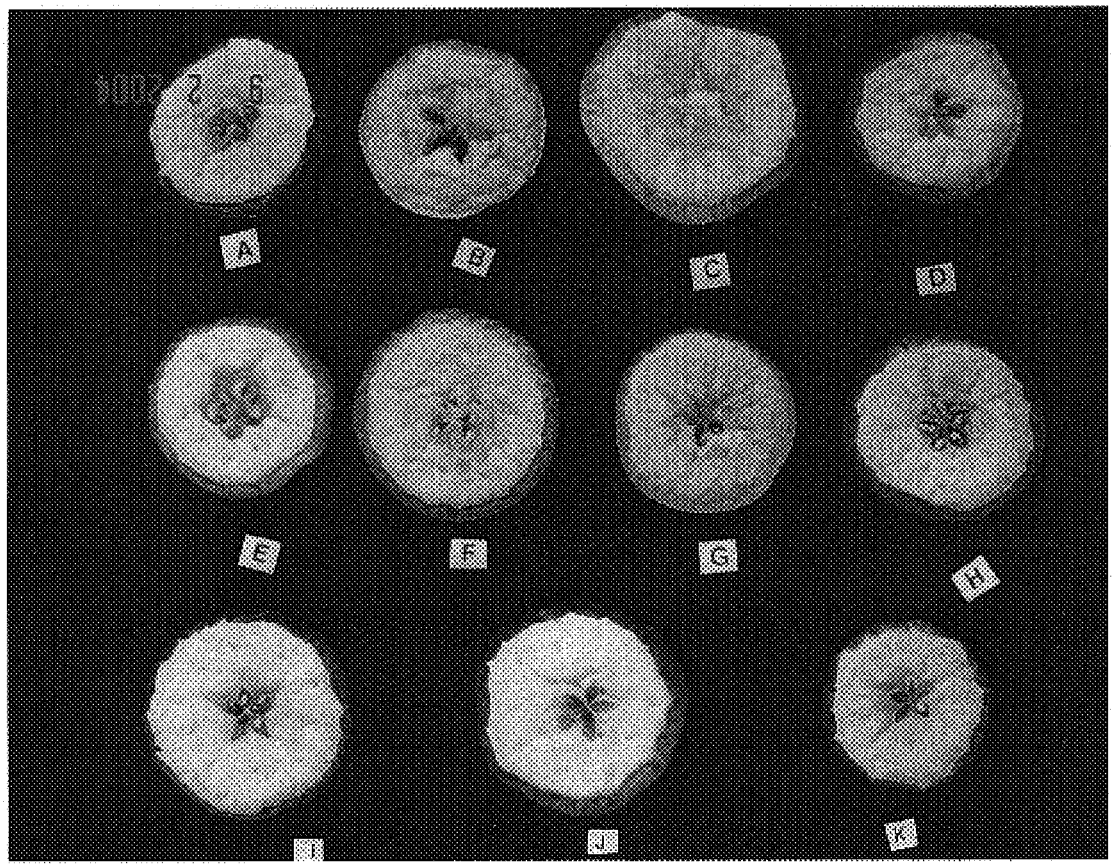
FIG. 5 shows the 'SJCA38R6A74' susceptibility to browning, 4 days after cutting at room temperature, as compared to other selected lines from AAFC ('SJCA649'; 'SCJA658', 'SJC7123-2') and to some industry standard cultivars ('Gala', 'Galarina', 'McIntosh Summerland', 'Reinette Russet', 'Spartan' and 'Cortland').

The following is a detailed description of 'SJCA38R6A74', a new and distinct cultivar of *Malus domestica*. It is based on observations made during several growing seasons, from 1999 to 2004, in L'Acadie and Frelighsburg and an apple orchard located in Mont Saint-Grégoire, Quebec. The colors are described using The Royal Horticultural Society (R.H.S.) Colour Chart.

Tree characteristics

Tree:

*Vigor.*—Intermediate.
*Branching habit* (*natural habit of an untrained, non-juvenile tree*).—Spreading drooping.
*Angle of bearing branches* (*with trunk*).—80–120°.
*Predominance of bearing* (*major fruit load*).—Both spur and shoots.

Shoot characteristics

Dormant one-year old shoot:

*Pubescence* (*on upper half*).—Medium.
*Shine of bark.*—Medium.
*Thickness* (*mm*) (*diameter at center of middle internode*).—Mean 3.3.
*Flexibility.*—Medium to strong.
*Length of internode* (*mm*) (*at middle third of shoot*).—Mean 24.7.
*Number of lenticels.*—Few to Medium (Mean 595).
*Size of lenticels.*—Small to Medium (Mean 0.7 mm).
*Predominant colour* (*on sunny side*).—Reddish-brown (RHS183A).
*Size of lateral bud.*—Large (Mean 9 mm).
*Shape of bud tip.*—Pointed.
*Position of bud relative to axis.*—Adpressed.
*Size of bud support.*—Small (Mean 1.5 mm).

Leaf characteristics

Shoot tip:

*Color of growing tip.*—White.
*Shape of leaves in cross section* (*leaves with petioles originating within* 2 *cm of the apical meristem*).—Concave to concave straight.
*Pubescence of upper side of leaves* (*leaves with petioles originating within* 2 *cm of the apical meristem*).—Very weak to weak.
*Coloration of lower side of leaves* (*leaves with petioles originating within* 2 *cm of the apical meristem*).—Green (RHS 145B).
*Distribution of color other than green* (*leaves with petioles originating within* 2 *cm of the apical meristem*).—None.

Leaf:

*Lobes.*—Absent.
*Shape.*—Oblong to slightly obovate.
*Orientation.*—Upwards outwards to Outwards.
*Length* (*measure of* $4^{th}$ *to* $6^{th}$ *fully expanded leaf*).—Mean 8.9.
*Width* (*measure of* $4^{th}$ *to* $6^{th}$ *fully expanded leaf*).—Mean 4.7.
*Ratio length/width of the blade* (*from* $4^{th}$ *to* $6^{th}$ *fully expanded leaf*).—1.9.
*Shape of apex.*—Mainly Acuminate with few Cuspidate.
*Shape of base.*—Cuneate to obtuse.
*Indentation of margin.*—Mainly serrate.
*Glossiness of upper side.*—Weak to medium.
*Pubescence on lower side.*—Nearly pubescent.
*Anthocyanin coloration of veins.*—Weak.
*Color of upper side.*—Dark green (RHS 147A).
*Intensity of anthocyanin coloration* (*of upper side*).—None.
*Length of petiole.*—3 to 6 cm.
*Size of stipule.*—Small when present (*Mean*4 *mm*).

Flower characteristics

Flowers:

*Time of bud burst.*—Medium.
*Calendar date of bud burst* (*silver tip*).—Apr. 21, 2004.
*Time of beginning of flowering* (10% *open flowers*).—May 14, 2004. (5 days before McIntosh in Freligsburg).
*Unopened flower: color of bud in full balloon stage* (*second or third flower bud when terminal flower is opening*).—Medium pink (63A).
*Unopened flower: color of bud* (*RHS color chart number*).—58A.
*Color of pedicel.*—Green (RHS 145B, opened flower); Red (RHS182A, unopened flower).
*Type of flower.*—Single.
*Size of flower* (*cm*) (*diameter when petals pressed in horizontal position*).—Mean 4.2.
*Shape of petal.*—Ovate.
*Position of margins of petal.*—Touching to Overlapping.
*Color of upper side of petal* (*RHS color chart number*).—Mainly white with a slight blush of 58A at fully open stage.
*Color of lower side of petal* (*RHS color chart number*).—Mainly white with irregular patterns of 58B at fully open stage.

Fruit characteristics

Fruit:

*Size* (*diameter*).—Medium to large (6 to 8 cm).
*Shape.*—Globose, Flat globose (oblate) and sometimes Lopsided.
*Symmetry in side view.*—Symmetric, and sometimes irregular (Lopsided).
*Ribbing.*—Present.
*Prominence of ribbing.*—Very weak.
*Crowning at distal end.*—Present.

*Degree of crowing at distal end.*—Weak.
*Aperture of eye.*—Closed to half open.
*Size of eye.*—Small to Medium (mean 6 mm).
*Persistence of calyx* (*in mature fruit*).—Present.
*Length of sepal.*—Medium (mean 5 mm).
*Spacing of sepals at base.*—Free to Touching.
*Depth of eye basin.*—Shallow to Shallow medium (mean 8 mm).
*Width of eye basin.*—Medium to Medium broad (mean 3 cm).
*Thickness of stalk.*—Thin to Medium (mean 2.2 mm).
*Length of stalk.*—Long (mean 2.4 mm).
*Depth of stalk cavity.*—Medium to Deep (mean 16 mm).
*Width of stalk cavity.*—Medium to Medium broad (mean 3.5 cm).
*Relief of surface.*—Smooth.
*Bloom of skin.*—7 on a scale of 1 to 9.
*Waxiness of skin.*—3 on a scale of 1 to 9.
*Translucency of skin.*—Absent.
*Thickness of skin.*—Medium to thick.
*Ground color of skin* (*fully mature fruit*).—Green-yellow (RHS 150C).
*Amount of over color skin.*—High to Very high.
*Over color of skin.*—Dark red (RHS 185A).
*Type of over color of skin.*—Washed out (faded) and Solid.
*Amount of russet.*—None.
*Position of russet.*—None.
*Number of lenticels.*—Low near the stem but very high near basin.
*Size of lenticels.*—Small to Medium.
*Prominence of lenticels* (*in contrast with skin*).—Intermediate prominence to prominent.
*Color of flesh.*—White.
*Distinctness of core line* (*median through locules*) *in cross-section.*—Absent or very weak.
*Aperture of locules in cross-section.*—Closed.
*Setting* (*yield efficiency*).—2.6 kg/cm$^2$ (Value based on four replicates using cumulative yield from 2000 to 2004).
*Maturity date.*—Medium.
*Seed color* (*at maturity*).—Brown to Dark brown (RHS 200B and A).
*Seed shape* (*at maturity*).—Long conic.

Fruit quality:

*Cracking tendency of skin/stem cavity.*—30% of samples were split at the stem cavity.
*Browning of flesh* (*one hour after being cut with stainless steel knife*).—Absent or very weak.
*Firmness of flesh* (*without skin — measurement with penetrometer*).—64 Newtons (Average of 10 fruits taken at two sides for a total of 20 measurements).
*Texture of flesh* (*when ripe*).—Fine.
*Grittiness.*—Absent.
*Juiciness.*—Medium to Juicy.
*Percentage of malic acid in fruit juice.*—Medium (0.5–0.9%) to High. (1.0–1.6%).
*Percentage of total sugars in fruit juice.*—Medium (11.5–13.4%).
*Flavor.*—Very aromatic, sweet and acidic at optimum maturity (around October 7, in Frelighsburg, QC).

Chemical analysis of the 'SJCA38R6A74' fruits reveal low levels of phenols, as compared to well-known varieties, as shown in Table 1 below. In particular, This confers to the fruit its "no-browning" characteristic several hours after being cut with a stainless steel knife, until completely dried at room temperature.

TABLE 1

Antioxidant composition, simple phenols and procyanidins of selected advanced apple lines compared to selected standard cultivars

| | | Simple Phenols | | | |
|---|---|---|---|---|---|
| Advanced lines & Cultivar | Total Phenoic Index (TPI) (μg/mL) | Chloro-genic acid (ug/mL) | Neo-chloro-genic acid (ug/mL) | P-coumaryl-quinic acid (ug/mL) | Total simple phenolics (ug/mL) |
| Gala | 230.8cde | 91.5c | 1.4ef | 12.8e | 105.7c |
| Galarina | 228.9cde | 29.5f | 38.4b | 1.3f | 69.2d |
| McIntosh | 274.3bc | 121.7b | 3.0de | 30.2b | 155.0b |
| Reinette Russet | 605.1a | 208.1a | 3.2cd | 31.3b | 242.6a |
| Spartan | 238.0cd | 95.1c | 1.8def | 11.2e | 108.1c |
| SJCA38R6A74 | 49.6g | 12.6g | 1.3ef | 20.3d | 34.2e |
| Cortland | 141.8f | 43.8ed | 1.8def | 25.1c | 70.7d |
| LSD | 49.0 | 12.3 | 1.7 | 4.2 | 15.8 |

| | Procyanidin | | | | | |
|---|---|---|---|---|---|---|
| Advanced lines & Cultivar | Pro-cyani-din B1 (ug/mL) | Cate-chin (ug/mL) | Pro-cyani-din B2 (ug/mL) | Epi-cate-chin (ug/mL) | Other Pro-cyani-dins (ug/mL) | Total pro-cyani-dins |
| Gala | 11.7e | 5.7cd | 41.6cd | 42.8cd | 9.3b | 111.1de |
| Galarina | 16.5d | 10.4bc | 57.4b | 55.3c | 4.0cd | 143.7cd |
| McIntosh | 9.7e | 8.8c | 42.0cd | 35.9de | 9.0b | 105.4de |
| Reinette Russet | 54.7a | 38.4a | 97.9a | 95.4a | 19.3a | 305.8a |
| Spartan | 0.0f | 11.2bc | 52.8bc | 46.5cd | 8.5bc | 119.1 cde |
| SJCA38R6A74 | 0.0f | 0.0d | 0.0e | 0.0g | 0.0d | 0.0g |
| Cortland | 0.0f | 8.3cd | 33.2d | 20.1f | 0.0d | 61.7f |
| LSD | 2.1 | 8.7 | 12.4 | 14.6 | 5.0 | 38.6 |

Antioxidant composition, dihydrochalcones of selected advanced apple lines compared to selected standard cultivars

| | Dihydrochalcones | | |
|---|---|---|---|
| Advanced lines & Cultivar | Phloretin-3-xyloglucoside | Phloridzin | Total Dihydrochalcones |
| Gala | 7.9de | 5.9cde | 13.9cd |
| Galarina | 11.3bc | 4.7de | 16.0c |
| McIntosh | 7.7ef | 6.1cd | 13.9cd |
| Reinette Russet | 41.2a | 15.6a | 56.8a |
| Spartan | 4.4g | 6.5c | 10.8def |
| SJCA38R6A74 | 10.9cd | 5.3cde | 15.3c |
| Cortland | 4.7g | 4.7de | 9.4g |
| LSD | 2.2 | 1.5 | 3.2 |

A letter appearing in association with more than one value in a column of Table 1, indicates that the values associated with that letter are not significantly different from each other i.e. they differ from less than the least significant difference (LSD).

The fruit has a long shelf life. It keeps its firmness, juiciness and flavor at standard cold room for 4–5 months. Given all its advantageous characteristics, the 'SJCA38R6A74' fruit is recommended for fresh eating, fruit salad and processing (dried apple chips).

Adaptation and Resistance to Diseases

'SCJA38R6A74' trees are hardy at Frelighsburg, Quebec (latitude 45° N., longitude 72° W.), where the average winter minimum temperature is −25° C. There has been no sign of powdery mildew (*Podosophaera leucotricha* (Ell. & Ev.) Salm.), fireblight (*Erwinia amylovora* (Burr.) Winslow et al.) or scab (*Venturia inaequalis*) infections on leaves during the evaluation period.

Figure 6:
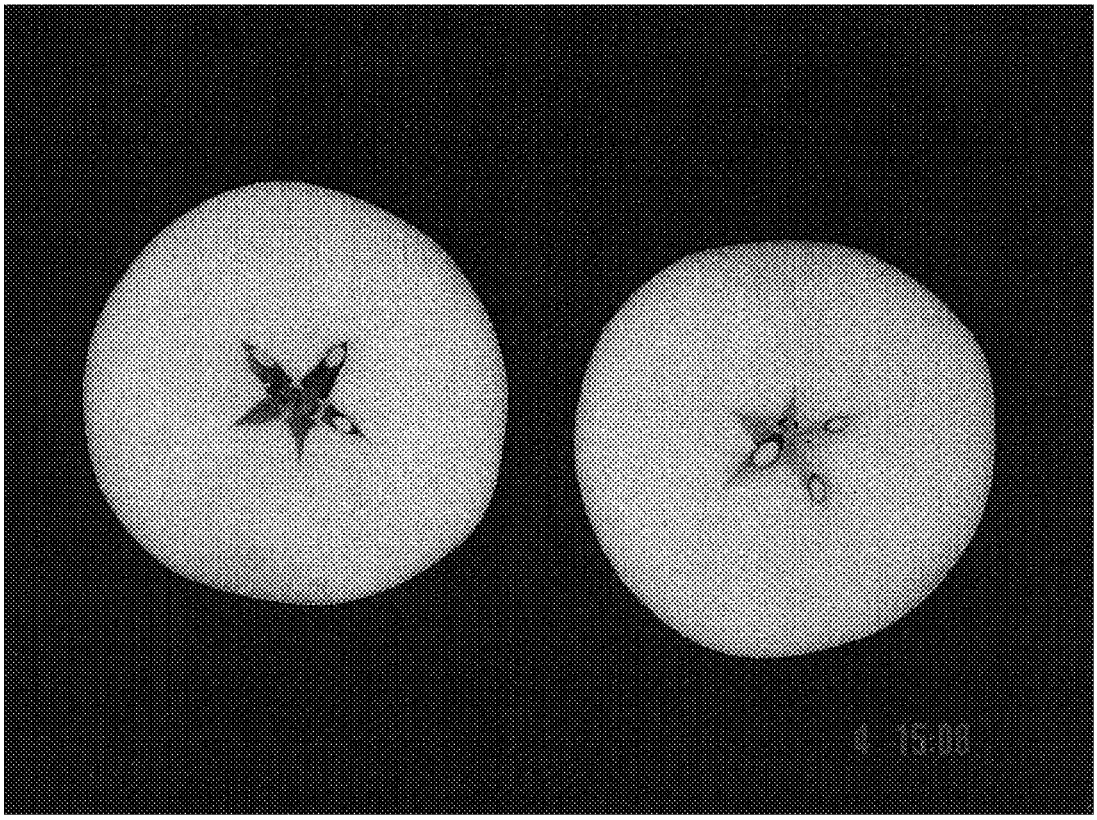
FIG. 6 shows bruising of the 'SJCA38R6A74' fruit after dropping.
Figure 7:
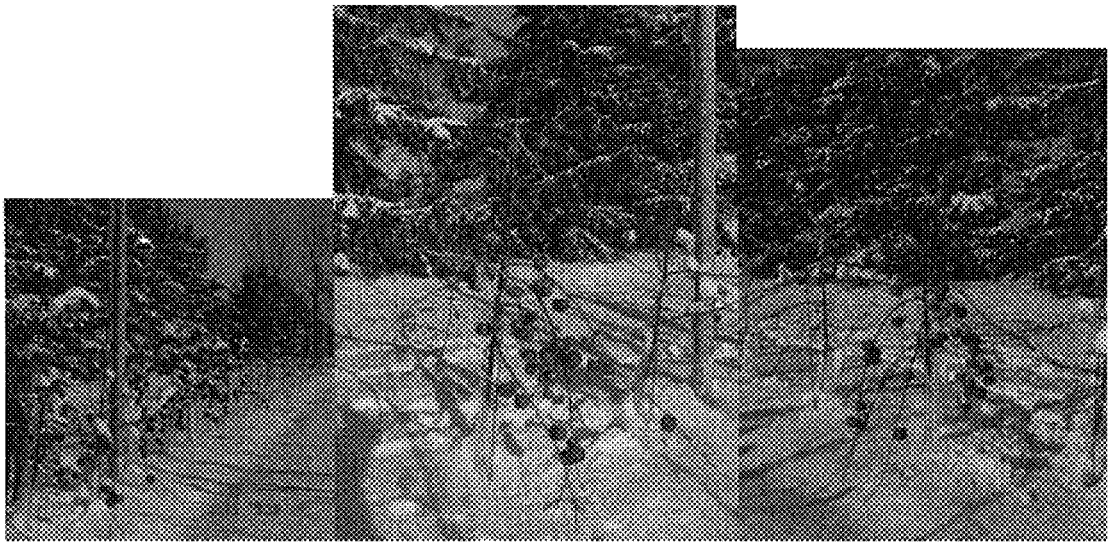
FIG. 7 shows the persistence of 'SJCA38R6A74' fruit on tree at maturity (photo taken on Dec. 15, 2004).

'SJCA38R6A74' fruits are susceptible to bitter pit, particularly if the season is dry and no irrigation is provided. The fruits are resistant to water core and the flesh does not turn brown after bruising (FIG. 6). As stated earlier, and contrary to 'McIntosh', the fruits of 'SJCA38R6A74' do not drop at maturity and stay on the tree even at −20° C. (FIG. 7), which makes it a good candidate for "Ice Cider" Production.

What is claimed is:

1. A new and distinct apple cultivar named 'SJCA38R6A74', substantially as described and illustrated herein.

* * * * *

Legend:
A=SJC649, B=SJC658, C=SJC7123-2, D=Gala, E=Galarina, F=McIntosh Summerland, G=Reinette Russet, H=Spartan, I=SJC7713-1, J=SJCA38R6A74, K=Cortland (Industry Standard)